US012642428B2

(12) United States Patent
Arieli et al.

(10) Patent No.: US 12,642,428 B2
(45) Date of Patent: Jun. 2, 2026

(54) OPTICAL DEVICE FOR INTRAOCULAR MEASUREMENTS

(71) Applicant: I-OPTSENS LTD., Jerusalem (IL)

(72) Inventors: Yoel Arieli, Jerusalem (IL); Shay Gilboa, Moshav Gimzo (IL); Boris Frenkel, Jerusalem (IL)

(73) Assignee: I-OPTSENS LTD., Jerusalem (IL)

( * ) Notice: Subject to any disclaimer, the term of this patent is extended or adjusted under 35 U.S.C. 154(b) by 678 days.

(21) Appl. No.: 18/000,873

(22) PCT Filed: Jun. 13, 2021

(86) PCT No.: PCT/IB2021/055196
§ 371 (c)(1),
(2) Date: Dec. 6, 2022

(87) PCT Pub. No.: WO2021/255611
PCT Pub. Date: Dec. 23, 2021

(65) Prior Publication Data
US 2023/0210358 A1      Jul. 6, 2023

Related U.S. Application Data

(60) Provisional application No. 63/128,200, filed on Dec. 21, 2020, provisional application No. 63/090,290, (Continued)

(51) Int. Cl.
*A61B 3/00*        (2006.01)
*A61B 3/16*        (2006.01)

(52) U.S. Cl.
CPC .............. *A61B 3/0008* (2013.01); *A61B 3/16* (2013.01)

(58) Field of Classification Search
CPC ................................ A61B 3/0008; A61B 3/16
(Continued)

(56) References Cited

U.S. PATENT DOCUMENTS 3,844,660 A      10/1974 Hunter
4,076,422 A      2/1978 Kohno
(Continued)

FOREIGN PATENT DOCUMENTS

AU        2017256924 A1      8/2018
CN        103487931 A        1/2014
(Continued)

OTHER PUBLICATIONS

Extended European Search Report for European Application No. 21825974.5 mailed May 28, 2024.
(Continued)

*Primary Examiner* — Sharrief I Broome
(74) *Attorney, Agent, or Firm* — Ballard Spahr LLP

(57)        ABSTRACT

Apparatus and methods are described including illumination equipment (300) configured to direct light into an eye of a subject. An optical device (100) is placed inside the subjects eye, the optical device including a Fabry Perot interferometer (106) comprising at least two mirrors (162, 164), the Fabry Perot interferometer (106) being configured such that a distance between the mirrors (162, 164) varies as an intraocular parameter of the subjects eye varies. A retroreflector (140) is configured such that light that is transmitted through the Fabry Perot interferometer (106) is automatically reflected out of the subjects eye. Readout equipment (400) is configured to detect the light that is reflected out of the subjects eye. Other applications are also described.

25 Claims, 9 Drawing Sheets

Related U.S. Application Data filed on Oct. 12, 2020, provisional application No. 63/038,834, filed on Jun. 14, 2020.

(58) Field of Classification Search
USPC ............................................ 351/221
See application file for complete search history.

(56) References Cited

U.S. PATENT DOCUMENTS

| | | | | |
|---|---|---|---|---|
| 5,217,015 | A * | 6/1993 | Kaye .................... | A61B 5/0002 |
| | | | | 600/587 |
| 7,639,367 | B2 | 12/2009 | Groot et al. | |
| 7,678,065 | B2 * | 3/2010 | Haffner .................... | A61B 3/16 |
| | | | | 600/587 |
| 9,417,147 | B2 | 8/2016 | Fischer et al. | |
| 2002/0052544 | A1 * | 5/2002 | Jeffries .................... | A61B 3/16 |
| | | | | 600/398 |
| 2003/0078487 | A1 * | 4/2003 | Jeffries .................... | A61B 3/16 |
| | | | | 600/398 |
| 2004/0254438 | A1 | 12/2004 | Chuck et al. | |
| 2013/0329232 | A1 | 12/2013 | Antila et al. | |
| 2017/0209045 | A1 | 7/2017 | Choo et al. | |
| 2017/0215727 | A1 * | 8/2017 | Chuck .................... | A61B 5/686 |
| 2018/0279876 | A1 * | 10/2018 | Paschalis ................. | A61B 3/16 |
| 2018/0344158 | A1 | 12/2018 | Hastings et al. | |
| 2019/0133442 | A1 | 5/2019 | Narasimhan et al. | |

FOREIGN PATENT DOCUMENTS

| | | |
|---|---|---|
| JP | H05141927 A | 6/1993 |
| JP | H09122075 A | 5/1997 |
| JP | 2013245981 A | 12/2013 |
| JP | 2019193680 A | 11/2019 |

OTHER PUBLICATIONS

International Search Report and Written Opinion from International Application No. PCT/IB2021/055196 mailed Aug. 31, 2021.

U.S. Appl. No. 63/038,834, filed Jun. 14, 2020.

U.S. Appl. No. 63/090,290, filed Oct. 12, 2020.

U.S. Appl. No. 63/128,200, filed Dec. 21, 2020.

Lee, et al., "A microscale optical implant for continuous in vivo monitoring of intraocular pressure", Microsystems & Nanoengineering, vol. 3, 2017, pp. 1-9.

Lee, et al., "Fabry-Perot optical sensor and portable detector for monitoring high-resolution ocular hemodynamics", IEEE Photonics Technol Lett. Author manuscript, 31(6), Mar. 15, 2019, pp. 1-12.

Lee, et al., "Nanoarray-Enhanced Implantable Intraocular Pressure Sensor With Remote Optical Readout", Solid-State Sensors, Actuators and Microsystems Workshop Hilton Head Island, South Carolina, Jun. 8-12, 2014, pp. 13-16.

Office Action for Japanese Application No. 2022-576829 mailed Apr. 8, 2025.

Office Action for Chinese Application No. 202180042684.X mailed on Jun. 14, 2025.

Office Action for Japanese Application No. 2022-576829 mailed Oct. 15, 2025.

Examination Report for Australian Application No. 2021291180 mailed Mar. 20, 2026.

* cited by examiner

FIG. 3

FP Gap (μm)

OPTICAL DEVICE FOR INTRAOCULAR MEASUREMENTS

CROSS-REFERENCES TO RELATED APPLICATIONS

The present application is a US national phase application of PCT Application No. PCT/IB2021/055196 to Arieli (published as WO 21/255611), filed Jun. 13, 2021, which claims priority from:

U.S. Provisional Patent Application 63/038,834 to Arieli, entitled "Optical measurement of intraocular pressure," filed Jun. 14, 2020;

U.S. Provisional Patent Application 63/090,290 to Arieli, entitled "Optical device for intraocular pressure measurement," filed Oct. 12, 2020; and U.S. Provisional Patent Application 63/128,200 to Arieli, entitled "Optical device for intraocular pressure measurement," filed Dec. 21, 2020.

Each of the above-referenced US Provisional applications is incorporated herein by reference.

FIELD OF EMBODIMENTS OF THE INVENTION

The present invention relates to systems and methods for intraocular measurements. Specifically, some applications of the present invention relate to intraocular pressure measurement and/or detection of substances inside the eye using an optical device.

BACKGROUND

Glaucoma is an eye disease which results in damage to the optic nerve and cause vision loss. The most common type is the open-angle glaucoma, which develops slowly over time and involves no pain. In open-angle glaucoma, vision is lost gradually, starting with peripheral vision and followed by central vision. Another type is closed-angle glaucoma, which can develop either gradually or suddenly, and may involve severe eye pain, blurred vision, mid-dilated pupil, redness of the eye, and/or nausea. Vision loss from glaucoma is permanent.

The risk factors for glaucoma include genetics, high intraocular pressure and high blood pressure. Although intraocular pressure higher than 21 mmHg or 2.8 kPa is often mentioned as leading to a greater risk, some may have high intraocular pressure for years and never develop damage.

There are many contact and non-contact methods for measuring intraocular pressure. One known method is the "Goldmann applanation tonometry", which is considered as the "gold standard" for intraocular pressure measurement. In this test, the eyes are anesthetized and dye is added to the eye. Then, a small tip is made to touch the surface of the eye and eye pressure is measured based on the force required to flatten a fixed area of the cornea. However, this test may be affected by the thickness and/or other biomechanical properties of the cornea.

In dynamic contour tonometry (DCT) contour matching is performed. A tip is pressed against the cornea, the tip containing a hollow portion having a similar shape to the cornea and having a pressure sensor at its center. The tip if designed to avoid deforming the cornea during measurement and it is therefore less influenced by the corneal thickness and other biomechanical properties. However, since the tip shape is designed for the shape of a normal cornea, it is more influenced by corneal curvature.

In rebound tonometers the intraocular pressure is determined by bouncing a small plastic tipped metal probe against the cornea.

In pneumotonometer measurements, the intraocular pressure is determined by utilizing a pneumatic sensor. Filtered air is pumped into a piston and travels through a small fenestrated membrane at one end that is placed against the cornea. The balance between the flow of air and the resistance to flow from the cornea affect the movement of the piston and this movement is used to calculate the intraocular pressure.

Non-contact tonometry uses a rapid air pulse to applanate or deform the cornea, and the corneal applanation is detected via an electro-optical system. Intraocular pressure is estimated by detecting the force of the air jet at the time of applanation or deformation.

The presence and/or concentration of various substances (such as glucose, amino acids, vitamins, electrolytes, etc.) within the eye, can be interpreted as markers for various physiological and/or medical conditions, such as the level of glucose within the subject's body, the existence of viruses, etc. Determining the presence and/or concentrations of such substances within the eye may be useful for determining a physiological and/or medical conditions of a patient.

SUMMARY OF EMBODIMENTS

In accordance with some applications of the present invention, an optical device (e.g., an optical element and/or an optical sensor) is placed at a location inside an eye of a subject, e.g., in the posterior and/or anterior chambers and/or the vitreous. For some applications, the optical device is attached to the ciliary muscles, the cornea, an intraocular lens, artificial cornea, or to any other portion inside the eye. Typically, the optical device is an optical sensor that is sensitive to the an intraocular parameter (such as, intraocular pressure) at its location within the eye such that optical characteristics of the optical sensor vary as the intraocular pressure varies.

Typically, the optical device includes a Fabry Perot interferometer and a retroreflector. Typically, the Fabry Perot interferometer includes two mirrors (which are typically semitransparent mirrors). Further typically, the Fabry Perot interferometer is configured such that, when the ambient pressure changes, the distance between the two mirrors of the interferometer changes. The Fabry Perot interferometer's spectral reflectance (e.g., its resonance frequency) changes too as a function of the distance between the two mirrors. Thus, when illumination equipment illuminates the Fabry Perot interferometer from outside the eye, the spectrum of the reflected light changes and this is detected in the signal detected by readout equipment which is also located outside the eye. A computer processor analyzes the reflected light to thereby derive the intraocular parameter.

Typically, the optical device includes a retroreflector, which is coupled to the Fabry Perot interferometer. In some cases, the direction of the optical axis of Fabry Perot interferometer may vary inside the eye such that (in the absence of the retroreflector) some rays that are incident upon the Fabry Perot interferometer are reflected such that the reflected rays do not coincide with the line connecting the eye pupil and the interferometer. By including the retroreflector, any ray that is incident upon and transmitted through the Fabry Perot interferometer, is reflected back in the direction that it came from and is again transmitted through the Fabry Perot interferometer on its reflection path. Thus, a ray that illuminates the Fabry Perot interferometer and is transmitted through the Fabry Perot interferometer is reflected back and directed to the readout equipment.

It is noted that in the absence of the retroreflector, the resonance frequency of the Fabry Perot interferometer would be transmitted through the optical device, rather than being reflected from the optical device. The computer processor would then have to determine the resonance frequency of the Fabry Perot interferometer by identifying troughs in the reflected light signal. Typically, it is more challenging to detect troughs in the reflected light signal than it is to identify peaks. As such, for some applications, including the retroreflector with the optical device facilitates the analysis of the reflected light signal by the computer processor, by making the resonance frequency of the interferometer more easily detectable.

For some applications, a reference optical device is coupled to the optical device such that optical axes of the optical device and the reference optical device are parallel to each other. Typically, the reference optical device has a generally similar structure to optical device. However, the walls defining the chamber that defines the gap between the Fabry Perot interferometer mirrors are all rigid, such that the distance between the reference Fabry Perot interferometer mirrors is constant. Since the distance between the Fabry Perot interferometer mirrors of reference optical device is constant, the reflected light signal from the reference optical device signal does not change as a function of the ambient pressure and it is typically used as a reference with which to calibrate the reflected light signal that is detected from optical device. In this manner, a computer processor is able to account for variations in the reflected light signal that is detected from the optical device that are caused by the angle of measurement between optical axis of the Fabry Perot interferometer and the readout equipment's optical axis. Alternatively or additionally, the computer processor is able to account for other optical effects in the eye in this manner.

For some applications, the optical device includes one or more additional Fabry interferometers in series with the Fabry Perot interferometer which is sensitive to ambient pressure changes. For some such applications, at least one of the additional Fabry Perot interferometers is configured such that the distance between its mirrors is constant. Since the distance between the mirrors of the additional Fabry Perot interferometer is constant, the reflected light signal from the additional Fabry Perot interferometer does not change as a function of the ambient pressure. For some applications, the additional Fabry Perot interferometer is used as a reference with which to calibrate the reflected light signal that is detected from the Fabry Perot interferometer which is sensitive to ambient pressure changes. Thus, in this manner the additional Fabry Perot interferometer functions as the reference optical device. As described above, using the reference optical device, a computer processor is able to account for variations in the reflected light signal that is detected from the optical device that are caused by the angle of measurement between optical axis of the Fabry Perot interferometer and the readout equipment's optical axis. Alternatively or additionally, the computer processor is able to account for other optical effects in the eye in this manner. In accordance with some applications of the present invention, an optical device is used for intraocular pressure measurements. For some applications, the optical device for intraocular pressure measurements is placed inside the eye of the subject. For some applications, the optical device is attached to the ciliary muscles, the cornea, an intraocular lens, artificial cornea, or to any other portion inside the eye, in front of or behind the pupil. For some applications, the optical device is sensitive to the intraocular pressure by virtue of its optical characteristics varying as a result of the intraocular pressure. For some applications, the optical device signal is read by means of illuminating the optical device from outside the eye and detecting the reflected light. For some applications, the optical device is illuminated from outside the eye using any electromagnetic wave source in any spectral range and/or any polarization state and/or any spectral bandwidth, and using a monochromatic, polychromatic, and/or a broadband light source. For some applications, the optical characteristics of the optical device that are changed due the intraocular pressure may change the intensity and/or spectrum and/or phase and/or polarization state of the reflected light. For some applications, the optical device signal is read by means of any known detecting device.

For some applications, additional optical elements such as a retroreflector, a mirror, and/or other known optical elements are placed inside the eye of the subject. For some applications, the optical elements are illuminated from outside the eye and the reflected light is detected. For some applications, the optical element is illuminated from outside the eye using any electromagnetic wave source in any spectral range and/or any polarization state and/or any spectral bandwidth, and using a monochromatic, polychromatic, and/or a broadband light source. For some applications, the optical characteristics of light reflected from the optical element (such as the intensity and/or spectrum and/or phase and/or polarization) is changed due to the presence and/or concentration of various substances inside the eye. For some applications, the presence of such substances and/or their concentration inside the eye are detected by analyzing the intensity and/or spectrum and/or phase and/or polarization of the reflected light. Alternatively or additionally, reflected light is detected when the subject's eyelids are closed. The optical characteristics of light reflected from the optical element (such as the intensity and/or spectrum and/or phase and/or polarization) is changed based upon parameters of blood within blood vessels within the subject's eyelids. This is because the eyelids are sufficiently thin for the incident light and the reflected light to pass through them, and in passing through the eyelids, the light typically passes through blood vessels within the eyelids. For some applications, one or more parameters of the subject's blood (such as oxygen saturation) are detected by analyzing the intensity and/or spectrum and/or phase and/or polarization of the reflected light.

There is therefore provided, in accordance with some applications of the present invention, apparatus including:

illumination equipment configured to direct light into an eye of a subject;

an optical device configured to be placed inside the subject's eye, the optical device including:

a Fabry Perot interferometer including at least two mirrors, the Fabry Perot interferometer being configured such that a distance between the mirrors varies as an intraocular parameter of the subject's eye varies; and a retroreflector configured such that light that is transmitted through the Fabry Perot interferometer is automatically reflected out of the subject's eye; and readout equipment configured to detect the light that is reflected out of the subject's eye.

In some applications, the apparatus is for use with an intraocular lens, and the optical device is configured to be coupled to the intraocular lens.

In some applications, the apparatus is for use with an intraocular lens, and the optical device is configured to be placed inside the subject's eye during a procedure in which the intraocular lens is placed in the subject's eye.

In some applications, the optical device is configured to be coupled to a ciliary body of the subject's eye.

In some applications, the Fabry Perot interferometer is configured such that the distance between the mirrors varies as intraocular pressure of the subject's eye varies.

In some applications, the Fabry Perot interferometer is configured such that the distance between the mirrors varies as intraocular temperature of the subject's eye varies.

In some applications, the optical device includes two or more additional mirrors, such that the optical device acts as a plurality of Fabry Perot interferometers in cascade.

In some applications, the apparatus further includes a computer processor that is configured to detect a parameter of blood of the subject by analyzing light that is reflected out of the subject's eye when an eyelid of the subject's eye is closed.

In some applications, the apparatus further includes a computer processor that is configured to analyze the light that is reflected out of the subject's eye such as to identify a resonance frequency of the Fabry Perot interferometer and to thereby determine the intraocular parameter of the subject's eye.

In some applications, the illumination equipment includes a swept monochromatic light source and the computer processor is configured to identify the resonance frequency of the Fabry Perot interferometer by detecting a frequency of light that is reflected out of the subject's eye.

In some applications, the illumination equipment includes a polychromatic light source having known spectral characteristics, and the computer processor is configured to identify the resonance frequency of the Fabry Perot interferometer based on the known spectral characteristics of the light source and a spectrum of the light that is reflected out of the subject's eye.

In some applications, the illumination equipment includes a broadband light source, and the computer processor is configured to identify the resonance frequency of the Fabry Perot interferometer by analyzing the spectrum of the light that is reflected out of the subject's eye by means of Fast Fourier Transform, to detect a distance between peaks in the reflected signal.

In some applications, the readout equipment is configured to detect light that is reflected out of the subject's eye that is at a resonance frequency of the Fabry Perot interferometer when an optical axis of the readout equipment is parallel with an optical axis of the illumination equipment.

In some applications, the readout equipment is configured to be moveable with respect to the illumination equipment, and the readout equipment is configured to detect light that is reflected out of the subject's eye that is not at the resonance frequency of the Fabry Perot interferometer when the optical axis of the readout equipment is not parallel with the optical axis of the illumination equipment.

In some applications, the apparatus further includes a computer processor that is configured to detect a presence and/or a concentration of a substance inside the subject's eye by analyzing light that is reflected out of the subject's eye when the optical axis of the readout equipment is not parallel with the optical axis of the illumination equipment.

In some applications, the apparatus further includes a reference Fabry Perot interferometer including at least two reference mirrors, a distance between the reference mirrors being fixed as the intraocular parameter of the subject's eye varies.

In some applications, the reference Fabry Perot interferometer is in series with the Fabry Perot interferometer that is configured such that the distance between its mirrors varies as the intraocular parameter of the subject's eye varies.

In some applications, the apparatus further includes a computer processor that is configured to analyze the light that is reflected out of the subject's eye and to account for changes in an angle between an optical axis of the optical device and an optical axis of the illumination equipment and/or the readout equipment, by calibrating measurements that are performed on light that is reflected from the Fabry Perot interferometer using measurements that are performed on light that is reflected from the reference Fabry Perot interferometer.

In some applications, the apparatus further includes a reference optical device coupled to the optical device, the reference optical device including the reference Fabry Perot interferometer.

In some applications, the reference optical device is coupled to the optical device such that optical axes of the optical device and the reference optical device are parallel to each other.

In some applications, the reference optical device includes a retroreflector configured such that light that is transmitted through the reference Fabry Perot interferometer is automatically reflected out of the subject's eye.

There is further provided, in accordance with some applications of the present invention, apparatus including:

illumination equipment configured to direct light into an eye of a subject;

an optical device configured to be placed inside the subject's eye, the optical device including a first Fabry Perot interferometer including at least two mirrors, the interferometer being configured such that a distance between the mirrors varies as an intraocular parameter of the subject's eye varies;

a reference Fabry Perot interferometer including at least two reference mirrors, a distance between the reference mirrors being fixed as the intraocular parameter of the subject's eye varies; and readout equipment configured to detect the light that is reflected out of the subject's eye.

In some applications, the reference Fabry Perot interferometer is in series with the first Fabry Perot interferometer.

In some applications, the first Fabry Perot interferometer is configured such that the distance between the mirrors varies as intraocular pressure of the subject's eye varies.

In some applications, the first Fabry Perot interferometer is configured such that the distance between the mirrors varies as intraocular temperature of the subject's eye varies.

In some applications, the optical device includes two or more additional mirrors, such that the optical device acts as a plurality of Fabry Perot interferometers in series with each other.

In some applications, the optical device further includes a retroreflector configured such that light that is transmitted through the first Fabry Perot interferometer is automatically reflected out of the subject's eye.

In some applications, the apparatus further includes a computer processor that is configured to detect a parameter of blood of the subject by analyzing light that is reflected out of the subject's eye when an eyelid of the subject's eye is closed.

In some applications, the apparatus further includes a reference optical device coupled to the optical device, the reference optical device including the reference Fabry Perot interferometer.

In some applications, the reference optical device is coupled to the optical device such that optical axes of the optical device and the reference optical device are parallel to each other.

In some applications, the reference optical device includes a retroreflector configured such that light that is transmitted through the reference Fabry Perot interferometer is automatically reflected out of the subject's eye.

In some applications, the apparatus further includes a computer processor that is configured to analyze the light that is reflected out of the subject's eye such as to identify a resonance frequency of the first Fabry Perot interferometer and to thereby determine the intraocular parameter of the subject's eye.

In some applications, the computer processor is configured to account for changes in an angle between an optical axis of the optical device and an optical axis of the illumination equipment and/or the readout equipment, by calibrating measurements that are performed on light that is reflected from the first Fabry Perot interferometer using measurements that are performed on light that is reflected from the reference Fabry Perot interferometer.

In some applications, the optical device further includes a retroreflector configured such that light that is transmitted through the first Fabry Perot interferometer is automatically reflected out of the subject's eye.

In some applications, the illumination equipment includes a swept monochromatic light source and the computer processor is configured to identify the resonance frequency of the first Fabry Perot interferometer by detecting a frequency of light that is reflected out of the subject's eye.

In some applications, the illumination equipment includes a polychromatic light source having known spectral characteristics, and the computer processor is configured to identify the resonance frequency of the first Fabry Perot interferometer based on the known spectral characteristics of the light source and a spectrum of the light that is reflected out of the subject's eye.

In some applications, the illumination equipment includes a broadband light source, and the computer processor is configured to identify the resonance frequency of the first Fabry Perot interferometer by analyzing the spectrum of the light that is reflected out of the subject's eye by means of Fast Fourier Transform, to detect a distance between peaks in the reflected signal.

In some applications, the readout equipment is configured to detect light that is reflected out of the subject's eye that is at a resonance frequency of the first Fabry Perot interferometer when an optical axis of the readout equipment is parallel with an optical axis of the illumination equipment.

In some applications, the readout equipment is configured to be moveable with respect to the illumination equipment, and the readout equipment is configured to detect light that is reflected out of the subject's eye that is not at the resonance frequency of the first Fabry Perot interferometer when the optical axis of the readout equipment is not parallel with the optical axis of the illumination equipment.

In some applications, the apparatus further includes a computer processor that is configured to detect a presence and/or a concentration of a substance inside the subject's eye by analyzing light that is reflected out of the subject's eye when the optical axis of the readout equipment is not parallel with the optical axis of the illumination equipment.

There is further provided, in accordance with some applications of the present invention, a method including:
directing light into an eye of a subject;
receiving reflected light from an optical device that is placed inside the subject's eye, and that includes:
a Fabry Perot interferometer that includes at least two mirrors, the Fabry Perot interferometer being configured such that a distance between the mirrors varies as an intraocular parameter of the subject's eye varies, and
a retroreflector configured such that light that is transmitted through the Fabry Perot interferometer is automatically reflected out of the subject's eye; and
analyzing the reflected light to thereby determine the intraocular parameter of the subject's eye.

There is further provided, in accordance with some applications of the present invention, a method including:
placing an optical device inside an eye of a subject, the optical device including:
a Fabry Perot interferometer that includes at least two mirrors, the Fabry Perot interferometer being configured such that a distance between the mirrors varies as an intraocular parameter of the subject's eye varies, and
a retroreflector configured such that light that is transmitted through the Fabry Perot interferometer is automatically reflected out of the subject's eye.

There is further provided, in accordance with some applications of the present invention, a method including:
directing light into an eye of a subject;
receiving reflected light from an optical device that is placed inside the subject's eye, and that includes a first Fabry Perot interferometer that includes at least two mirrors, the Fabry Perot interferometer being configured such that a distance between the mirrors varies as an intraocular parameter of the subject's eye varies, and
receiving reflected light from a reference Fabry Perot interferometer that includes at least two reference mirrors, a distance between the reference mirrors being fixed as the intraocular parameter of the subject's eye varies; and
analyzing the reflected light from the first Fabry Perot interferometer and the reflected light from the reference Fabry Perot interferometer to thereby determine the intraocular parameter of the subject's eye.

There is further provided, in accordance with some applications of the present invention, a method including:
placing an optical device inside an eye of a subject, the optical device including a first Fabry Perot interferometer that includes at least two mirrors, the first Fabry Perot interferometer being configured such that a distance between the mirrors varies as an intraocular parameter of the subject's eye varies, and
placing inside the subject's eye a reference Fabry Perot interferometer that includes at least two reference mirrors, a distance between the reference mirrors being fixed as the intraocular parameter of the subject's eye varies.

The present invention will be more fully understood from the following detailed description of embodiments thereof, taken together with the drawings, in which:

BRIEF DESCRIPTION OF THE DRAWINGS

FIG. 3 is a schematic illustration of a top view of a flexible membrane attached to a mirror, in accordance with some applications of the present invention;

DETAILED DESCRIPTION OF EMBODIMENTS

Figure 1:
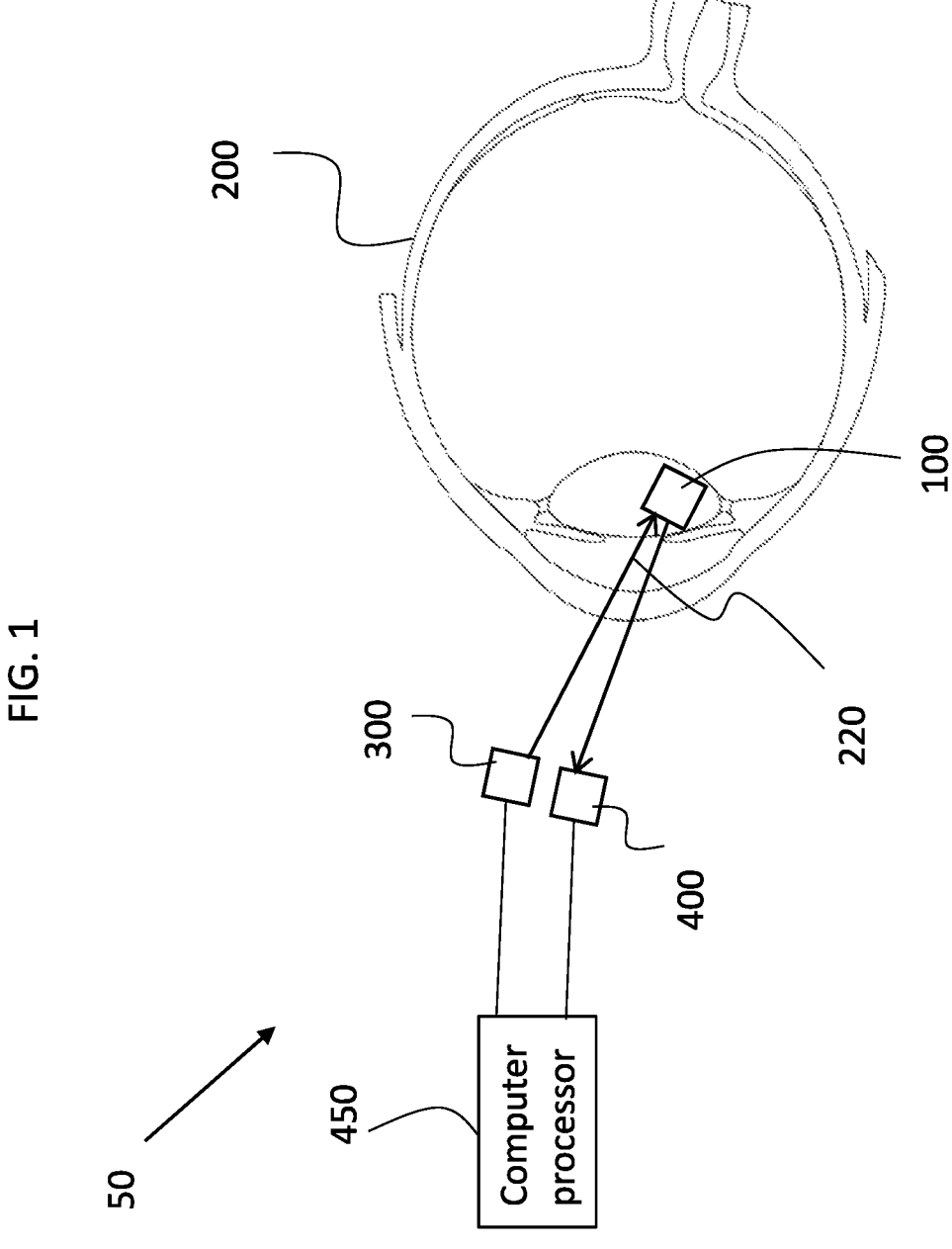
FIG. 1 is a schematic illustration of an optical system for measuring intraocular pressure, in accordance with some applications of the present invention.

Reference is now made to FIG. 1, which is a schematic illustration of an optical system 50 for measuring intraocular pressure, in accordance with some applications of the present invention. Typically, at least one optical device 100 (e.g., an optical element and/or an optical sensor) is placed at a location inside an eye 200 of a subject, e.g., in the posterior and/or anterior chambers and/or the vitreous. For some applications, the optical device is attached to the ciliary muscles, the cornea, an intraocular lens, artificial cornea, or to any other portion inside the eye. Typically, optical device 100 is an optical sensor that is sensitive to the intraocular pressure at its location within the eye such that optical characteristics of the optical sensor vary as the intraocular pressure varies. Alternatively or additionally, optical device 100 includes one or more types of optical elements, such as a mirror, a retroreflector, a polarizer, and/or any other type of optical element and/or optical system that is configured to reflect light that is directed toward the optical device.

For some applications, optical device 100 is injected into the eye (for example, using a dedicated syringe). For some such applications, the optical device is coupled to a portion of the subject's eye (such as the ciliary muscles) using a coupling element (such as a pin, a barb, and/or a suture) and/or using a biocompatible adhesive. For some applications, the optical device is coupled to an intraocular lens (not shown). Alternatively or additionally, the optical device is implanted into the subject's eye as part of a cataract procedure, in which in intraocular lens is implanted in the subject's eye.

Typically, illumination equipment 300 illuminates the optical device from outside the eye (e.g., through pupil 220). Further typically, the illumination equipment includes one or more light sources (such as an LED, a laser, a monochromatic light source, a swept light source, a polychromatic light source, and/or a broadband light source). For some applications, the illumination equipment includes additional optical elements, such as lenses, polarizers, etc. Readout equipment 400 typically detects the light that is reflected back from the optical device 100 (e.g., through the pupil 220). Typically, the readout equipment includes an optical detector, such as a camera, a light intensity sensor, and/or a spectrometer. For some applications, the apparatus includes a beam splitter that is configured to direct reflected light toward the optical detector. Typically, the illumination equipment and/or the readout equipment communicates with a computer processor 450. For example, the computer processor may drive the illumination equipment to illuminate the optical device, and/or the computer processor may analyze the light that is reflected back from the optical device and that is detected by readout equipment 400.

As described above, typically, optical device 100 is an optical sensor that is sensitive to the intraocular pressure at its location within the eye such that optical characteristics of the optical sensor vary as the intraocular pressure varies. Therefore, the signal detected by readout equipment 400 typically varies in accordance with variations in the intraocular pressure at the location of the optical device 100. The variations in the signal detected by readout equipment 400 may include changes in any one of the intensity, the spectrum, the polarization, and/or the phase of the signal detected by readout equipment 400. By analyzing the optical characteristics of the signal detected by readout equipment 400 the computer processor is typically configured to determine the intraocular pressure of the eye.

For some applications, optical device 100 includes one or more types of optical elements, such as a mirror, and/or a retroreflector, etc., that are configured to reflect light that is directed toward the optical device. For some such applications, the optical characteristics of the signal detected by readout equipment 400 (such as the intensity, the spectrum, the polarization, and/or the phase of the signal) vary based on the presence and/or concentration of various substances inside the eye. By analyzing the optical characteristics of the signal detected by readout equipment 400 the computer processor is typically configured to detect the presence and/or concentration of various substances inside the eye. For some such applications, based upon the above-described analysis, the computer processor is configured to deduce various physiological and medical conditions of the subject, such as the subject's blood sugar level, the presence and/or concentration of a virus, amino acids, vitamins. For some applications, the computer processor is thereby configured to derive a physiological and/or medical condition of the subject that affects the presence and/or concentration of such substances.

Figure 2:
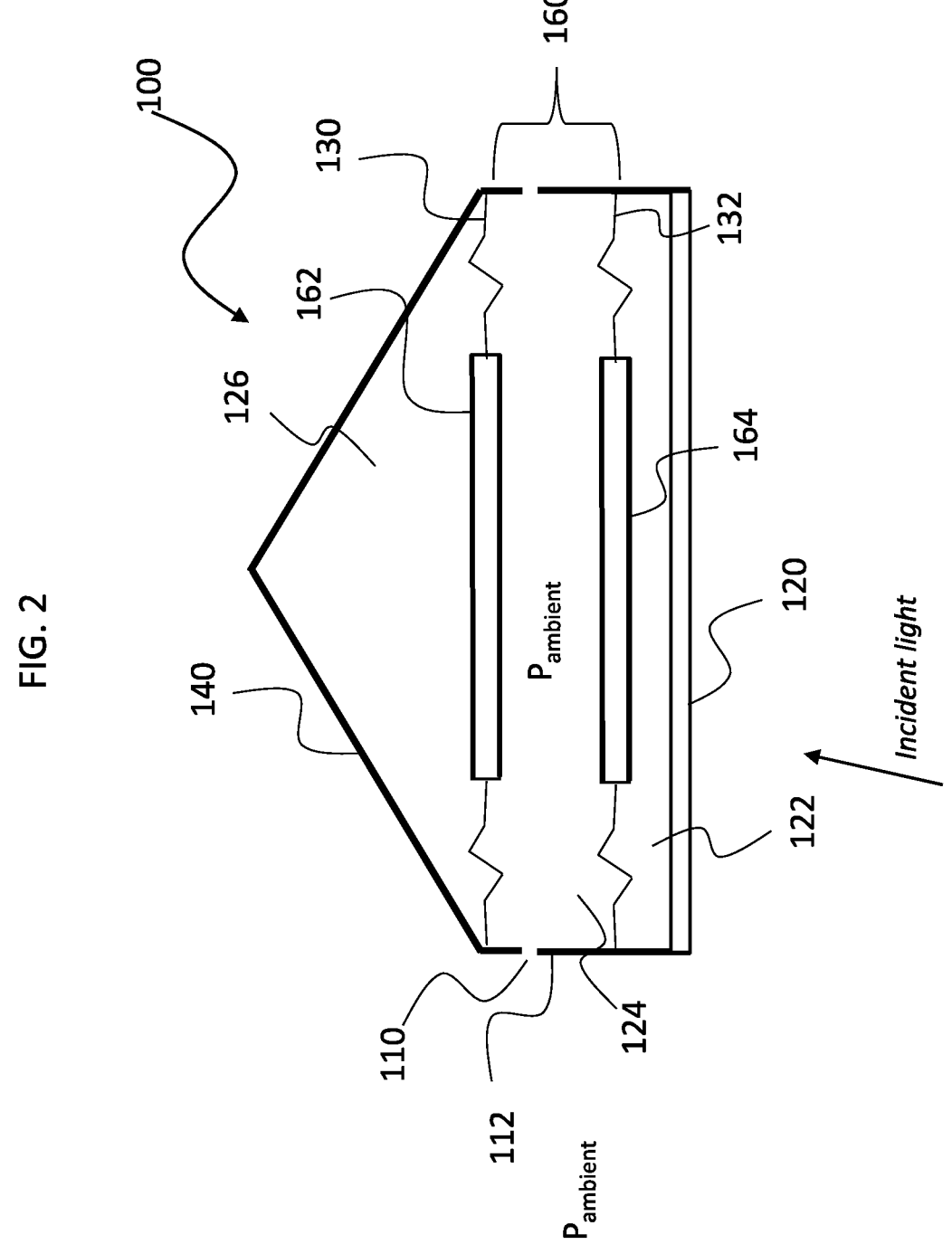
FIG. 2 is a schematic illustration of an optical device for measuring intraocular pressure, in accordance with some applications of the present invention.

Alternatively or additionally, reflected light is detected by readout equipment when the subject's eyelids are closed. For some such applications, the optical characteristics of the signal detected by readout equipment 400 (such as the intensity, the spectrum, the polarization, and/or the phase of the signal) vary based upon parameters of blood within blood vessels within the subject's eyelids. This is because the eyelids are sufficiently thin for the incident light and the reflected light to pass through them, and in passing through the eyelids, the light typically passes through blood vessels within the eyelids. By analyzing the optical characteristics of the signal detected by readout equipment 400 the computer processor is typically configured to determine one or more parameters of the subject's blood (such as oxygen saturation), e.g., by analyzing the intensity and/or spectrum and/or phase and/or polarization of the reflected light. For some such applications, based upon the above-described analysis, the computer processor is configured to deduce various physiological and medical conditions of the subject. Reference is now made to FIG. 2, which is a schematic illustration of optical device 100, in accordance with some applications of the present invention. Typically, incident light (which is directed from illumination equipment 300 into the eye via the eye pupil) enters the optical device via a window 120, which is typically transparent. For some applications, the optical device includes a Fabry Perot interferometer 160 and a retroreflector 140. Typically, the Fabry Perot interferometer includes two mirrors 162, 164 (which are typically semitransparent mirrors). The two mirrors 162, 164 are typically attached to flexible membranes 130 and 132 that are parallel to each other. For example, one surface of each of the membranes may be coated with a semi-transparent reflective coating (with a membrane that is coated in this manner being described herein as an example of a semi-transparent mirror), a mirror (e.g., a semi-transparent mirror) may be coupled to a central region of each of the membranes, or a mirror (e.g., a semi-transparent mirror) may be disposed on a central region that is cut out of the flexible membranes. For some applications, both surfaces of the each of the membranes are coated with a semi-transparent reflective coating, or a semi-transparent mirror is stuck to both surfaces of each of the membranes. In this manner, chamber 124 acts as a plurality of Fabry Perot interferometers in cascade.

For some applications, additional portions of the optical device are coated with a reflective coating (e.g., a semi-transparent reflective coating) and/or have a mirror (e.g., a semi-transparent mirror) coupled to them, such that the optical device includes a plurality of pairs of mirrors, and thereby acts as a plurality of Fabry Perot interferometers in series with each other. For example, window 120 may be coated on both sides with semitransparent reflective coating, or a semitransparent mirror may be coupled to each side of window 120, such that window 120 acts as a Fabry Perot interferometer, and the optical device acts as a plurality of Fabry Perot interferometers in series with each other. In general, the scope of the present application includes an optical device which includes additional mirrors to mirrors 162, 164, such that the optical device acts as a plurality of Fabry Perot interferometers in series with each other. It is noted that, for such applications, the plurality of Fabry Perot interferometers do not necessarily have the same characteristics as each other. Typically, this generates additional data, which the computer processor analyzes such as to derive properties of the eye (such as intraocular pressure), relative to if the optical device includes only a single Fabry Perot interferometer. It is noted however that the scope of the present application includes an optical device that includes only a single Fabry Perot interferometer. For some applications, one or more of the additional Fabry Perot interferometers is configured to act as a reference optical device, as described in further detail hereinbelow with reference to FIG. 8.

Typically, at least one of the two membranes 130 and 132 is sealed with respect to gas and fluid. For some applications, in addition to defining walls of chamber 124, the two membranes 130 and 132 define walls of chambers 122 and 126. Typically, the two membranes 130 and 132 constitute flexible walls for the three chambers 122, 124 and 126, while other walls of the chambers (e.g., side walls 112 of the chambers) are typically rigid. For example, the membranes may be disposed inside a rigid housing 166 that defines side walls of the chambers. Chambers 122 and 126 are typically sealed and filled with a fluid (e.g., a gas or a liquid) that is transparent and flexible.

For some applications, chamber 124 is sealed and filled with a fluid (e.g., a gas or a liquid). Alternatively, chamber 124 is open to the ambient conditions by means of one or more openings 110 (e.g., an opening in side wall 112 of the chamber, as shown), such that pressure in chamber 124 is approximately equal to ambient pressure $P_{ambient}$. Accordingly, when the ambient pressure changes, the distance between the two interferometer's mirrors 162 and 164 changes. The Fabry Perot interferometer's spectral reflectance (e.g., its resonance frequency) changes too as a function of the distance between the two mirrors. Thus, when illumination equipment 300 (shown in FIG. 1) illuminates the Fabry Perot interferometer from outside the eye, the spectrum of the reflected light changes and this is detected in the signal detected by readout equipment 400 (shown in FIG. 1) which is also located outside the eye.

Typically, the optical device includes retroreflector 140, which is coupled to the Fabry Perot interferometer 160. Further typically, the retroreflector is disposed on the far side of the optical device relative to the side of the optical device at which window 120 is disposed. For some applications, a corner cube retroreflector is used, as shown. Alternatively or additionally, a different type of retroreflector is used, such as cat eye retroreflector. In some cases, the direction of the optical axis of Fabry Perot interferometer 160 may vary inside the eye such that (in the absence of the retroreflector) some rays that are incident upon the Fabry Perot interferometer are reflected such that the reflected rays do not coincide with the line connecting the eye pupil and the interferometer. By including the retroreflector, any ray that is incident upon and transmitted through the Fabry Perot interferometer, is reflected back in the direction that it came from and is again transmitted through the Fabry Perot interferometer on its reflection path. Thus, a ray that illuminates the Fabry Perot interferometer and is transmitted through the Fabry Perot interferometer is reflected back and directed to the readout equipment. For some applications, a beam splitter (not shown) is added to direct the reflected ray to the readout equipment. For some applications, retroreflector 140 is manufactured as part of the optical device such that chamber 126 is defined by membrane 130 and the retroreflector (i.e., such that the retroreflector defines wall(s) of chamber 126). For some such applications, membrane 130 is a rigid membrane. Alternatively, the retroreflector is a stand-alone device that is coupled to the Fabry Perot interferometer (e.g., behind chamber 126). For some applications, the retroreflector provides additional advantages, for example, as described hereinbelow with reference to FIG. 9.

Figure 3:
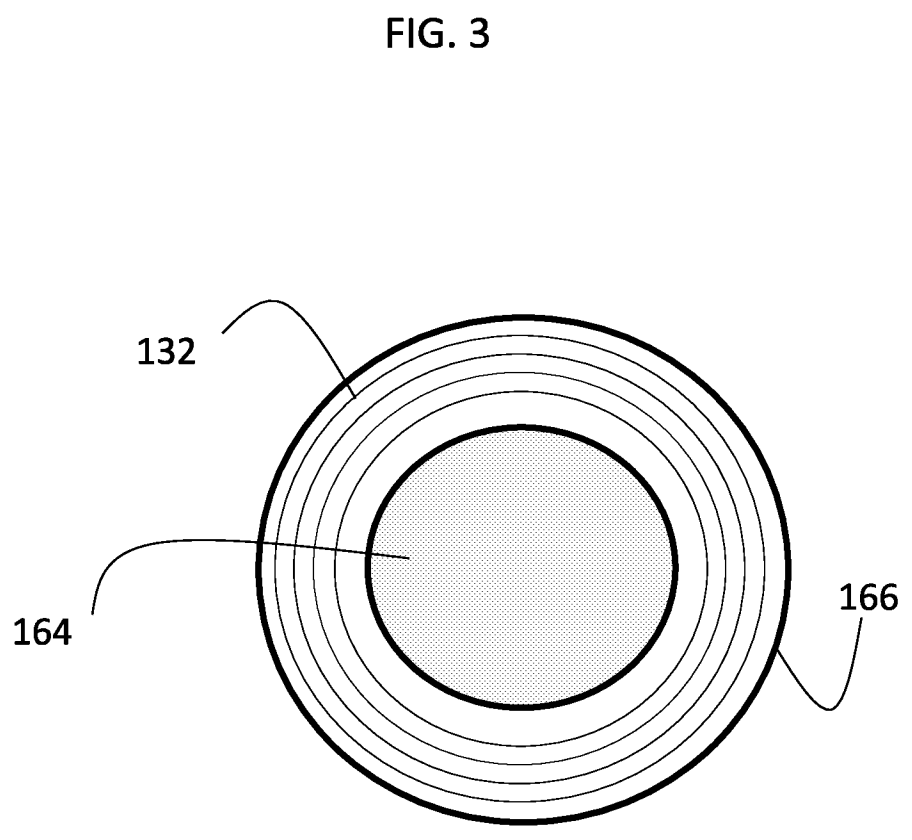

Reference is now made to FIG. 3, which is a schematic illustration of flexible membrane 132 and mirror 164, in accordance with some applications of the present invention. As described hereinabove, for some applications, membrane 132 is disposed inside a rigid housing 166. For some applications, the outer edge of the membrane is coupled to the inside of the rigid housing. For some applications, membrane 132 consists of a flexible material (e.g., a wavy sheet of flexible material). For some applications, mirror 164 is a flat sheet that is coupled to a central region of membrane 132. Alternatively, a central region of the membrane is cut out, and the mirror is disposed at the central region of the membrane. Typically, membrane 130 and mirror 162 have generally similar structures to that of membrane 132 and mirror 164. For some applications, only one membrane out of membranes 130 and 132 is flexible and the other membrane is rigid, such that only one of the two membranes moves in response to changes in the ambient pressure. Typically, a change in the pressure difference between the two surfaces of each of the membranes causes the membrane to become distorted, such that the distance between the mirrors is changed.

Figure 4:
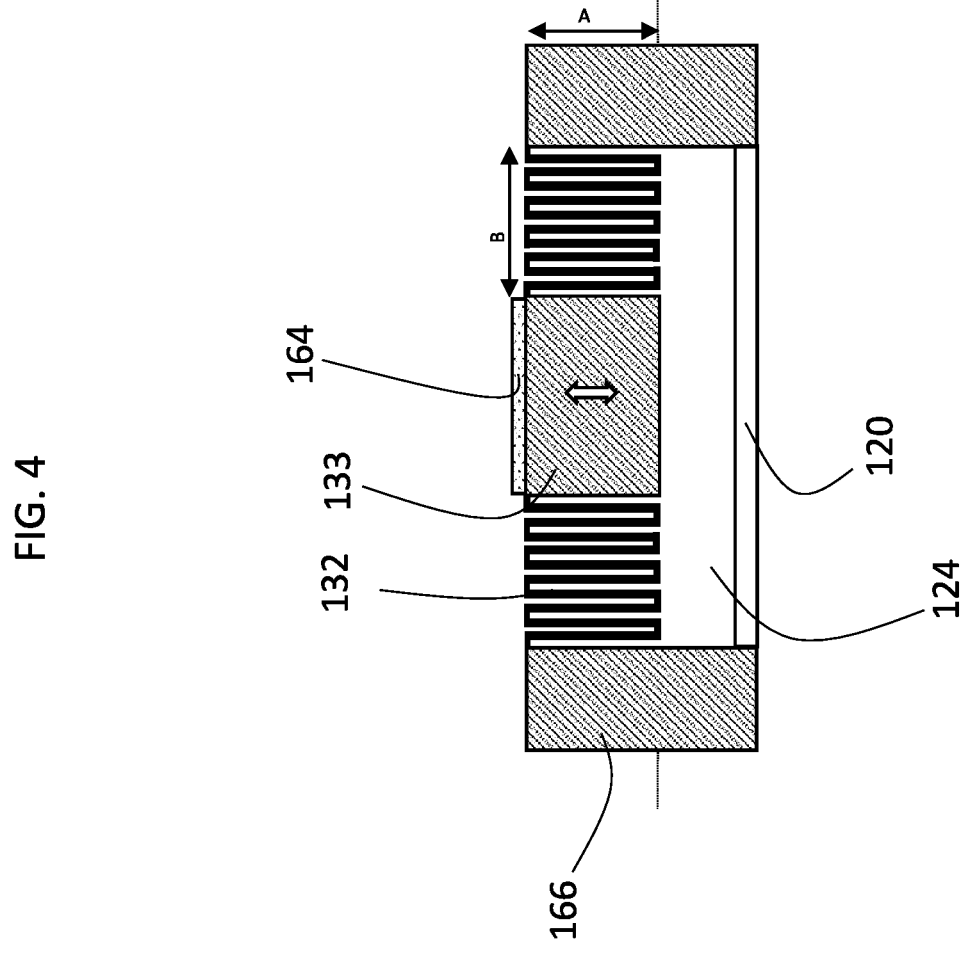
FIG. 4 is a schematic illustration of a flexible membrane attached to a mirror, in accordance with some applications of the present invention.

Reference is now made to FIG. 4, which is a schematic cross-sectional illustration of flexible membrane 132 and mirror 164, in accordance with some applications of the present invention. In this embodiment, membrane 132 is attached to the rigid housing 166 of the optical device shown in FIG. 2. The membrane 132 consists of an accordion shape, made of a flexible material. A semitransparent mirror or a semitransparent reflective coating is typically disposed on an inner and/or an outer surface of a central region 133 of the flexible membrane, which has a flat shape. Typically, membrane 132 and mirror 164 have generally similar structures to that of membrane 130 and semitransparent mirror 162. Typically, a change in the pressure difference between the two surfaces of each of the membranes causes the membrane to become distorted, such that the distance between the semitransparent mirrors is changed.

Figure 5:
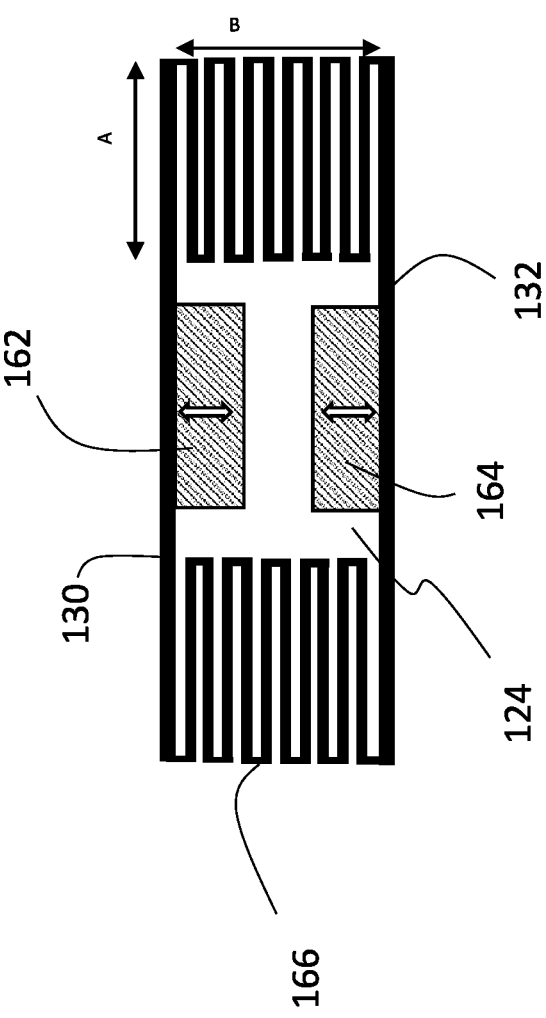
FIG. 5 is a schematic illustration of a Fabry Perot interferometer, in accordance with some alternative applications of the present invention.

Reference is now made to FIG. 5, which is a schematic cross-sectional illustration of Fabry Perot interferometer 160, in accordance with some applications of the present invention. For some applications, membrane 130 and/or membrane 132 is rigid and flat, and housing 166 is flexible, for example, having an accordion shape, and being made of a flexible material. A semitransparent mirror or a semitransparent coating is typically disposed on an inner and/or an outer surface membrane 130 and 132. A change in the pressure difference between the inner pressure of the chamber 124 and the outside pressure distorts housing 166, and thus the distance between the semitransparent mirrors.

Figure 6:
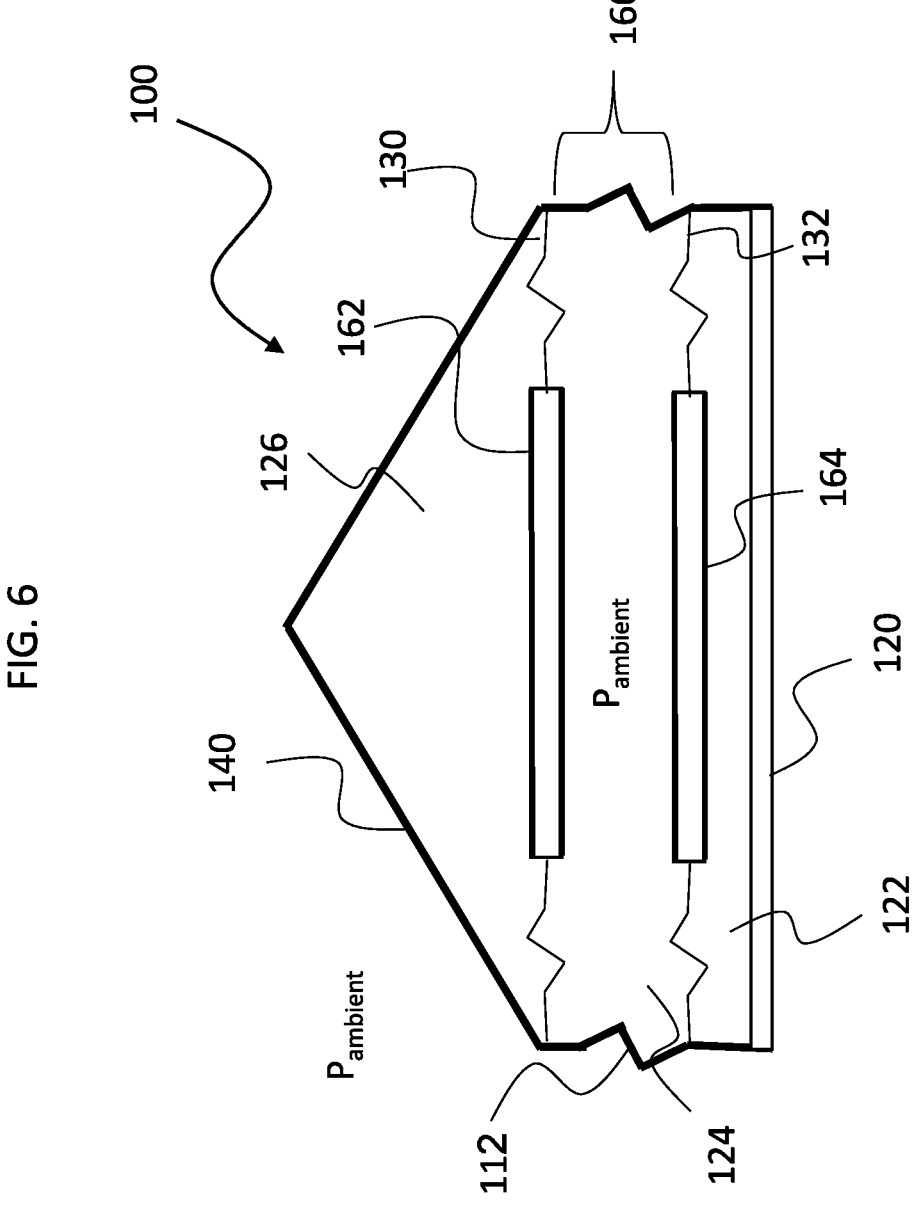
FIG. 6 is a schematic illustration of an optical device for measuring intraocular pressure, in accordance with some applications of the present invention.

It should be noted that the present application is not limited to the specific embodiments of Fabry Perot interferometer 106 that are shown and/or described herein. For example, the embodiments of FIGS. 4 and 5 may be combined such that both the membranes 130, 132 and the housing 166 have accordion shapes and/or are flexible (e.g., as shown in FIG. 6). Similarly, the scope of the present application includes an accordion shape having any number of folds (or periods), any shape (including a varying shape between different periods), varying frequencies and sizes between periods. Similarly, the thickness of the membranes or of the housing may be different from each other, may vary, and may be any thickness.

Reference is now made to FIG. 6, which is a schematic illustration of optical device 100, in accordance with some applications of the present invention. Optical device 100 as shown in FIG. 6 is generally similar to that shown in FIG. 2, but in the embodiment shown in FIG. 6, chamber 124 is sealed. For some applications, the side walls 112 of chamber 124 (or a portion thereof) are flexible, and do not define opening 110 (opening 110 being shown in FIG. 1). Chamber 124 is typically sealed and filled with a fluid (e.g., a gas or a liquid) that is transparent and flexible. Accordingly, when the ambient pressure changes, the side walls change their structure and the distance between the two interferometer's mirrors 162 and 164 changes. As described hereinabove, optical device typically includes retroreflector 140, the function of the retroreflector being as described hereinabove with reference to FIG. 2 and/or as described hereinbelow with reference to FIG. 9. For some applications, the optical device includes a beam splitter (not shown), to direct the reflected ray to the readout equipment.

Figure 7:
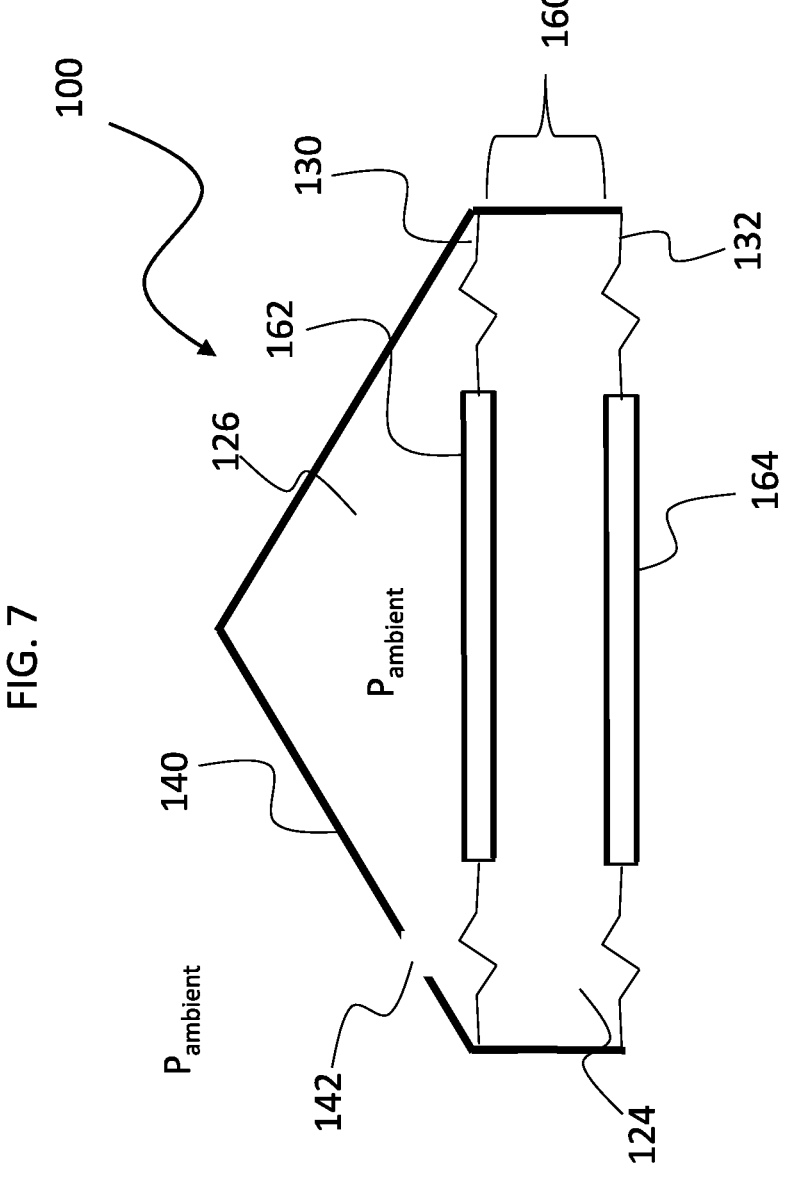
FIG. 7 is a schematic illustration of an optical device for measuring intraocular pressure, in accordance with some alternative applications of the present invention.

Reference is now made to FIG. 7, which is a schematic illustration of optical device 100, in accordance with some applications of the present invention. Optical device 100 as shown in FIG. 7 is generally similar to that shown in FIG.

2, but in the embodiment shown in FIG. 7, is no window 120 between mirror 164 and front of the optical device. Chamber 124 is typically sealed and filled with a fluid (e.g., a gas or a liquid) that is transparent and flexible. At least one of the two membranes 130 and 132 is flexible. Typically, for such applications, chamber 126 (disposed behind chamber 124 relative to the illumination equipment) is open to the ambient conditions, e.g., via opening 142. Accordingly, when the ambient pressure changes, the distance between the two interferometer's mirrors 162 and 164 changes. As described hereinabove, optical device typically includes retroreflector 140, the function of the retroreflector being as described hereinabove with reference to FIG. 2 and/or as described hereinbelow with reference to FIG. 9. For some applications, the optical device includes a beam splitter (not shown), to direct the reflected ray to the readout equipment.

In accordance with the above description the scope of the present application includes an optical device that has any number of Fabry Perot interferometers. Typically, at least one of the Fabry Perot interferometers (Fabry Perot interferometer 106) has a resonance frequency that is dependent upon ambient pressure. The mirrors of the Fabry Perot interferometer having a resonance frequency that is dependent upon ambient pressure are typically disposed on membranes 130 and 132, which define two walls of chamber 124 that are parallel to each other. The distance between the walls of the chamber may be made to be dependent upon ambient pressure by virtue of membrane 130 being flexible, and/or membrane 132 being flexible, and/or the side walls of chamber 124 being flexible. For some applications, chamber 124 defines an opening thereto (e.g., opening 110, shown in FIG. 2), such that distance between the walls of chamber 124 is sensitive to ambient pressure. The mirrors of the Fabry Perot interferometers may include semitransparent mirrors and/or membranes that are covered in a semitransparent reflective coating.

Figure 8:
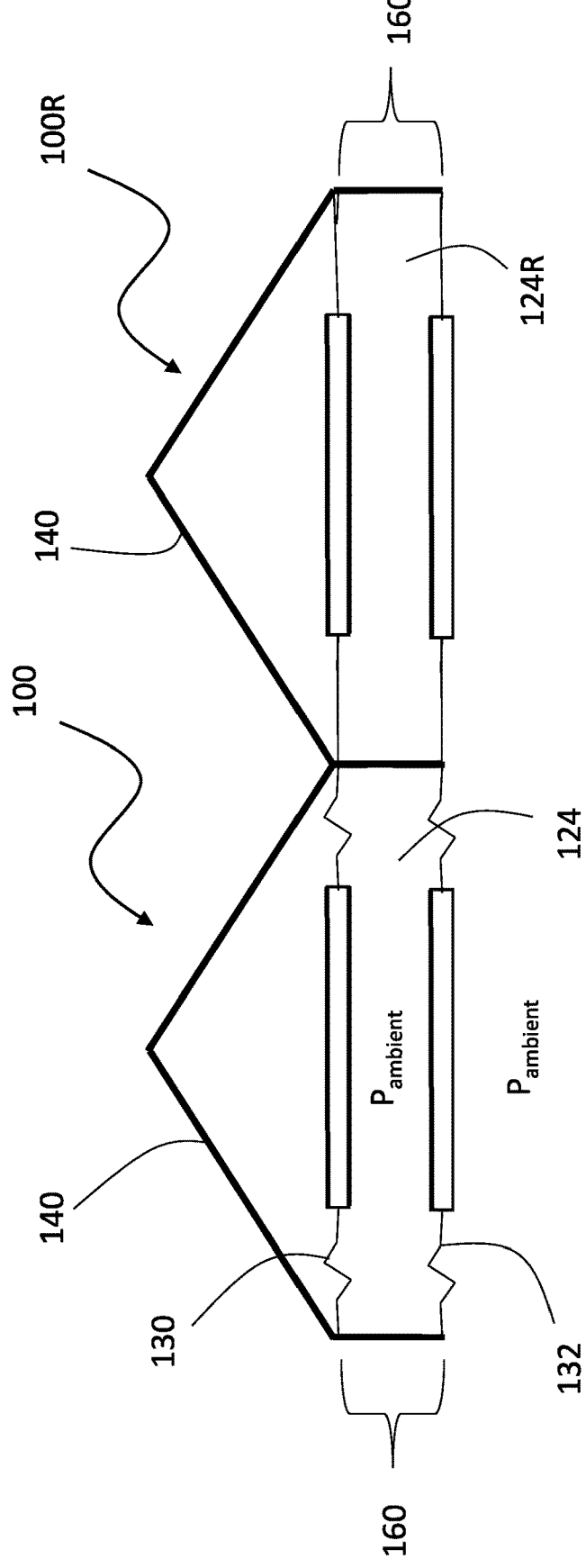
FIG. 8 is a schematic illustration of an optical device for measuring intraocular pressure with a reference optical device coupled thereto, in accordance with some applications of the present invention.

Reference is now made to FIG. 8, which is a schematic illustration of optical device 100 for measuring intraocular pressure with a reference optical device 100R coupled thereto, in accordance with some applications of the present invention. For some applications, the reference optical device is coupled to the optical device such that optical axes of the optical device and the reference optical device are parallel to each other. Typically, optical device 100 has a structure and function that is as described hereinabove, with at least some of the walls of chamber 124 (i.e., the chamber that defines the gap between the Fabry Perot interferometer mirrors) being flexible, such that the distance between the Fabry Perot interferometer mirrors varies as the ambient intraocular pressure varies. For example, as shown membranes 130 and 132 of optical device 100 are flexible. Typically, reference optical device 100R has a generally similar structure to optical device 100. However, the walls defining chamber 124R (i.e., the chamber that defines the gap between the Fabry Perot interferometer mirrors, which is the equivalent to chamber 124 of optical device 100) are all rigid, such that the distance between the reference Fabry Perot interferometer mirrors is constant. Both optical device 100 and reference optical device 100R typically include retroreflector 140, the function of the retroreflector being as described hereinabove with reference to FIG. 2 and/or as described hereinbelow with reference to FIG. 9.

Since the distance between the Fabry Perot interferometer mirrors of reference optical device 100R is constant, the reflected light signal from the reference optical device 100R signal does not change as a function of the ambient pressure and it is typically used as a reference with which to calibrate the reflected light signal that is detected from optical device 100. In this manner, the computer processor is able to account for variations in the reflected light signal that is detected from optical device 100 that are caused by the angle of measurement between optical axis of the Fabry Perot interferometer and the readout equipment's optical axis. Alternatively or additionally, the computer processor is able to account for other optical effects in the eye in this manner. For some applications, in order for the computer processor to be able to distinguish between the reflected light signal from optical device 100 and the reflected light signal from optical device 100R, each of the optical device includes a polarizers that generates a respective polarization state, and the computer processor measures the polarization states of the reflected light signals to determine which signal is from optical device 100 and which signal is from reference optical device 100R. Alternatively, the two different wavelength bandwidths are used in order to enable the computer processor to distinguish between the reflected light signal from optical device 100 and the reflected light signal from optical device 100R.

As described hereinabove, for some applications, the optical device includes one or more additional Fabry interferometers in series with Fabry Perot interferometer 106 (which is sensitive to ambient pressure changes). For some such applications, at least one of the additional Fabry Perot interferometers is configured such that the distance between its mirrors is constant. Since the distance between the mirrors of the additional Fabry Perot interferometer is constant, the reflected light signal from the additional Fabry Perot interferometer does not change as a function of the ambient pressure. For some applications, the additional Fabry Perot interferometer is used as a reference with which to calibrate the reflected light signal that is detected from Fabry Perot interferometer 106 (which is sensitive to ambient pressure changes). Thus, in this manner, the additional Fabry Perot interferometer functions as the reference optical device. As described above, using the reference optical device, a computer processor is able to account for variations in the reflected light signal that is detected from the optical device that are caused by the angle of measurement between optical axis of Fabry Perot interferometer 106 and the readout equipment's optical axis. Alternatively or additionally, the computer processor is able to account for other optical effects in the eye in this manner.

The scope of the present application includes combining any one of the embodiments of optical device 100 described herein with a reference optical device 100R, in accordance with the description of FIG. 8, mutatis mutandis.

Figure 9:
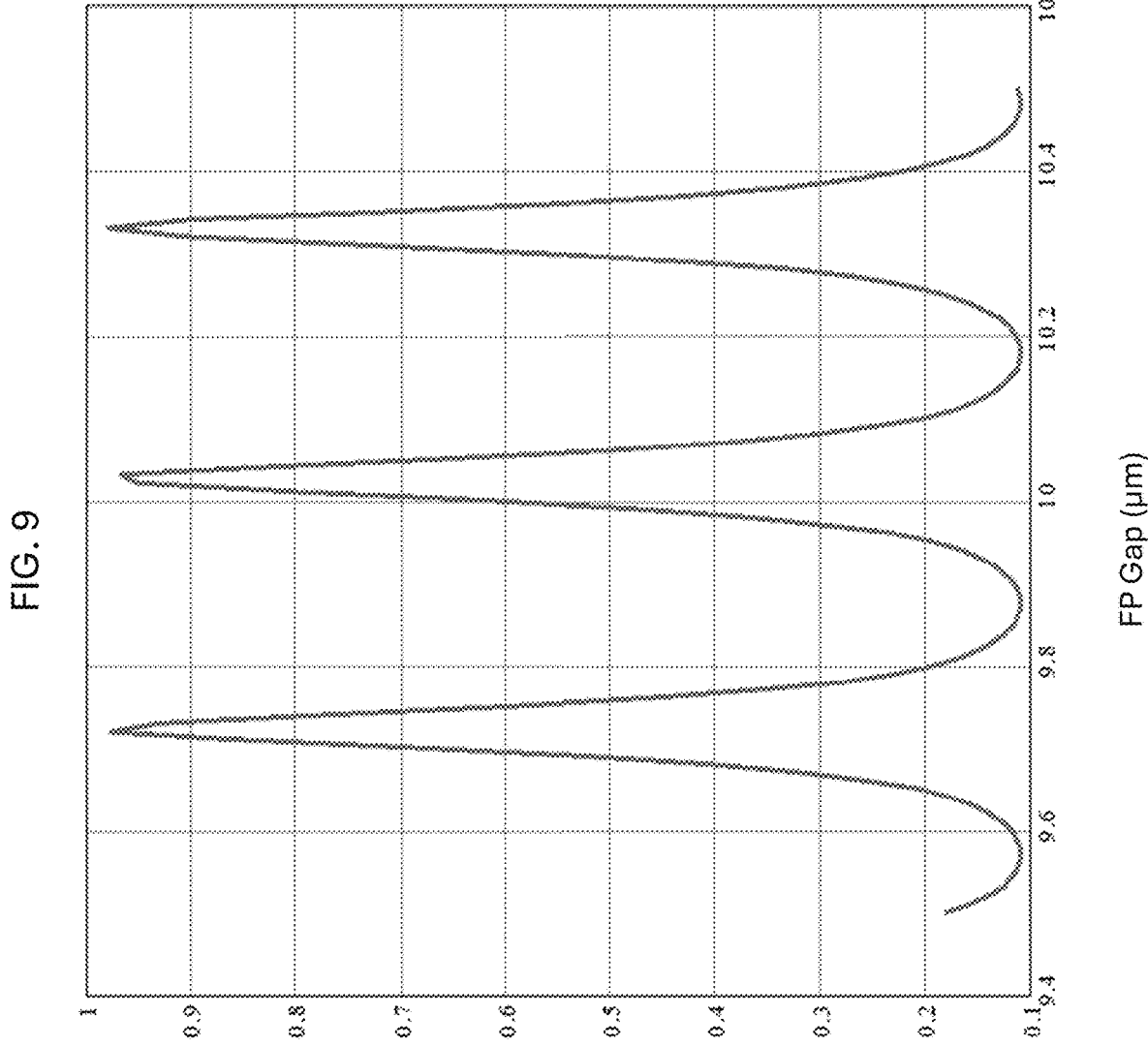
FIG. 9 is a graph showing the typical spectral profile of a light signal that is detected by readout equipment, in accordance with some applications of the present invention.

Reference is now made to FIG. 9, which is a graph showing the typical spectral profile of a light signal (i.e. intensity versus frequency) that is detected by readout equipment for a given distance between the two mirrors of a Fabry Perot interferometer that includes a retroreflector, in accordance with some applications of the present invention. As described hereinabove, typically, optical device 100 includes a retroreflector, which is configured to return the light signal that is transmitted through the interferometer to the readout equipment. When the optical axis of the optical device is not aligned with the optical axes of the illumination and readout equipment, light that is not transmitted through the Fabry Perot interferometer is typically reflected to a different reflection angle, in accordance with the laws of reflection. Therefore, as shown in FIG. 9, when the optical axis of the optical device is not aligned with the optical axes of the illumination and readout equipment, and when a broadband light source is used, this typically results in the reflected light signal including a plurality of peaks, which indicate the resonance frequency of the Fabry Perot interferometer, and on the basis of which the computer processor is configured to derive the distance between the mirrors of the interferometer, to thereby determine intraocular pressure and/or other intraocular parameters. It is noted that in the absence of the retroreflector, the resonance frequency of the Fabry Perot interferometer would be transmitted through the optical device, rather than being reflected from the optical device. The computer processor would then have to determine the resonance frequency by identifying troughs in the reflected light signal. Typically, it is more challenging to detect troughs in the reflected light signal than it is to identify peaks. As such, for some applications, including the retroreflector with the optical device facilitates the analysis of the reflected light signal by the computer processor, by making the resonance frequency of the interferometer more easily detectable.

The scope of the present application includes combining any one of the embodiments of optical device 100 described herein with a retroreflector 140, in accordance with the description of FIGS. 2 and 9, mutatis mutandis.

Typically, as the distance between the two mirrors of the Fabry Perot interferometer varies, the distance between peaks in the reflected signal varies (whether in terms of frequency or wavelength). Typically, the distance between the peaks in the reflected signal also varies as a function of the angle $\theta$ between the optical axis of the Fabry Perot interferometer and the optical axis of the illumination and readout equipment since the effective distance between the two mirrors is now $d_{eff}=d \cos \theta$. For small angles and/or small distances, this effect may be neglected. For some applications, reference optical device 101 is coupled to optical device 100, such that this effect can be accounted for, as described hereinabove with reference to FIG. 8.

As described hereinabove, illumination equipment 300 typically includes a light source, such as an LED, a laser, a monochromatic light source, a swept light source, a polychromatic light source, and/or a broadband light source. Typically, when a monochromatic light source is used, the monochromatic light source is a swept monochromatic light source that varies the frequency of the light over time. Typically, the computer processor detects at which transmission frequency the light is reflected from the optical device such as to derive the resonance frequency of the Fabry Perot interferometer, to thereby determine intraocular pressure and/or other intraocular parameters.

Typically, when a polychromatic light source having a limited bandwidth is used, there is a single peak in the reflected signal. The peak of the Fabry Perot interferometer reflected signal scans the optical frequencies of the illumination and the spectrum of reflected light changes. Typically, the computer processor detects the change in the spectrum of the reflected light, either by spectral measurements or intensity measurements. Further typically, the light source has known spectral characteristics, and based on the known spectral characteristics of the light source and the spectrum of the reflected light, the computer processor derives the resonance frequency of the Fabry Perot interferometer, to thereby determine intraocular pressure and/or other intraocular parameters.

Typically, when a broadband illumination source with a relatively large bandwidth is used, the number of spectral peaks in the Fabry Perot interferometer reflected signal that are within the illumination source bandwidth are detected. Typically, by counting this number the computer processor is able to perform a large dynamic range of pressure measurements. For some such applications, the computer processor analyzes the spectrum of the reflected light by means of Fast Fourier Transform, in order to detect the frequency of peaks in the reflected signal (i.e., the spectral distance between peaks in the reflected signal), to derive the resonance frequency of the Fabry Perot interferometer, and thereby determine intraocular pressure and/or other intraocular parameters.

It is noted that, typically, the optical device is calibrated such that the relationship between the resonance frequency of the Fabry Perot interferometer and respective intraocular pressures (and/or other intraocular parameters) is known. Thus, the computer processor typically performs a calculation that automatically outputs the intraocular pressure (and/or other intraocular parameters), rather than performing a first calculation to derive the resonance frequency of the Fabry Perot interferometer, and a separate calculation to thereby determine intraocular pressure and/or other intraocular parameters.

It is noted that the graph shown in FIG. 9 is representative of one method of analyzing the signal that is outputted by optical device 100, whereby the analysis is based on spectral analysis of the signal. However, the scope of the present application includes other types of analysis, such as phase analysis, intensity analysis, etc., mutatis mutandis. Such alternative types of analysis are typically applicable to cases in which optical device 100 includes a plurality of Fabry Perot interferometers in series with each other, as described hereinabove. For example, in cases in which optical device 100 includes a plurality of Fabry Perot interferometers in series with each other, the computer processor may determine the intensity and or spectrum of the reflected light signal, to derive the resonance frequency of the Fabry Perot interferometer, and thereby determine intraocular pressure and/or other intraocular parameters.

Typically, other light wavelengths that are not at the resonance frequency of the Fabry Perot interferometer are reflected by the front mirror of the Fabry Perot interferometer, in accordance with the laws of reflection. Further typically, in order to perform the Fabry Perot interferometer measurements as described above, the axes of the illumination equipment and the readout equipment are parallel with each other. Thus, unless the optical axis of the Fabry Perot interferometer coincides the axis of illumination, other light wavelengths are reflected elsewhere and do not propagate to the eye's pupil and to the readout equipment. For some applications, the direction of the optical axis of the readout equipment relative to the illumination equipment is varied, such that other light wavelengths that are not at the resonance frequency of the Fabry Perot interferometer are reflected by the front mirror of the Fabry Perot interferometer, such that they are detected by the readout equipment and analyzed by the computer processor. Typically, by analyzing the intensity and/or spectrum and/or phase and/or polarization of the reflected wavelengths the presence and/or concentration of various substances inside the eye are be detected. By analyzing this data, various physiological and medical conditions can be deduced, such as the level of sugar, the existence of viruses, amino acids, vitamins and any physiological and medical conditions that affect the existence of the substances and/or their concentrations. Alternatively or additionally, reflected light is detected by readout equipment when the subject's eyelids are closed. For some such applications, the optical characteristics of the signal detected by readout equipment 400 (such as the intensity, the spectrum, the polarization, and/or the phase of the signal) vary based upon parameters of blood within blood vessels within the subject's eyelids. This is because the eyelids are sufficiently thin for the incident light and the reflected light to pass through them, and in passing through the eyelids, the light typically passes through blood vessels within the eyelids. By analyzing the optical characteristics of the signal detected by readout equipment 400, the computer processor is typically configured to determine one or more parameters of the subject's blood (such as oxygen saturation), e.g., by analyzing the intensity and/or spectrum and/or phase and/or polarization of the reflected light. For some such applications, based upon the above-described analysis, the computer processor is configured to deduce various physiological and medical conditions of the subject.

It is noted that any optical sensor having optical characteristics that are sensitive to intraocular pressure and/or other intraocular parameters may be used to perform one or more of the above-described analyses. For example, a retroreflector and/or a mirror can be used in optical device 100. The presence and/or concentration of various substances inside the eye may be detected by analyzing the intensity and/or spectrum and/or phase and/or polarization of the reflected wavelengths. The measurements may be repeated in different directions and/or different light sources and/or spectral range and/or polarizations and/or bandwidths. For some applications, an optical device that is configured to perform intraocular pressure measurements is combined with an additional optical device that is configured to detect the presence and/or concentration of various substances inside the eye, and the combined device may be placed inside a subject's eye.

For some applications, the apparatus and methods described herein are used to detect an alternative or an additional intraocular parameter. For example, the apparatus and methods described herein may be used to detect intraocular temperature, and the Fabry Perot interferometer may be configured such that the distance between the mirrors of the interferometer changes in a detectable manner in response to changes in the ambient temperature. For example, materials with different expansion coefficients may be used within the Fabry Perot interferometer, such that the distance between the mirrors of the interferometer changes in a detectable manner in response to changes in the ambient temperature. For some applications, an optical device that is configured in this manner is placed in the eye together with a reference optical device 100R, in accordance with the description of FIG. 8, mutatis mutandis. For some applications, an optical device that is configured in this manner is placed in the eye together with a retroreflector 140, in accordance with the description of FIGS. 2 and 9, mutatis mutandis.

For some applications, alternative or additional optical elements are used within optical device 100. For example, the optical device may include one or more of the following optical elements, by way of illustration and not limitation:

a. One or more lenses in order to focus the illumination light and/or to image the light source on the Fabry Perot interferometer.

b. One or more polarizers to accommodate the polarization of the illumination and/or the reflected light in order to increase the signal-to-noise ratio in the measurement and/or to separate between the signal from the optical device 100 and signal form reference optical device 100R.

c. One or more beam splitters to direct the illumination and/or reflected light to different directions.

For some applications, the apparatus and methods described herein are used to detect the pressure of a different portion of a body of a subject, and/or to detect the pressure of a different element. For example, the apparatus and methods described herein may be used to detect pressure in an industrial setting.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising:
illumination equipment configured to direct light into an eye of a subject;
an optical device configured to be placed inside the subject's eye, the optical device comprising:
a Fabry Perot interferometer comprising at least two mirrors, the Fabry Perot interferometer being configured such that a distance between the mirrors varies as an intraocular parameter of the subject's eye varies; and
a retroreflector configured such that light that is transmitted through the Fabry Perot interferometer is automatically reflected out of the subject's eye; and
readout equipment configured to detect the light that is reflected out of the subject's eye.

2. The apparatus according to claim 1, wherein the apparatus is for use with an intraocular lens, and wherein the optical device is configured to be coupled to the intraocular lens.

3. The apparatus according to claim 1, wherein the optical device is configured to be coupled to a ciliary body of the subject's eye.

4. The apparatus according to claim 1, wherein the Fabry Perot interferometer is configured such that the distance between the mirrors varies as intraocular pressure of the subject's eye varies.

5. The apparatus according to claim 1, wherein the Fabry Perot interferometer is configured such that the distance between the mirrors varies as intraocular temperature of the subject's eye varies.

6. The apparatus according to claim 1, wherein the optical device comprises two or more additional mirrors, such that the optical device acts as a plurality of Fabry Perot interferometers in cascade.

7. The apparatus according to claim 1, further comprising a computer processor that is configured to analyze the light that is reflected out of the subject's eye such as to identify a resonance frequency of the Fabry Perot interferometer and to thereby determine the intraocular parameter of the subject's eye.

8. The apparatus according to claim 7, wherein the illumination equipment includes a swept monochromatic light source and wherein the computer processor is configured to identify the resonance frequency of the Fabry Perot interferometer by detecting a frequency of light that is reflected out of the subject's eye.

9. The apparatus according to claim 7, wherein the illumination equipment includes a polychromatic light source having known spectral characteristics, and wherein the computer processor is configured to identify the resonance frequency of the Fabry Perot interferometer based on the known spectral characteristics of the light source and a spectrum of the light that is reflected out of the subject's eye.

10. The apparatus according to claim 7, wherein the illumination equipment includes a broadband light source, and wherein the computer processor is configured to identify the resonance frequency of the Fabry Perot interferometer by analyzing the spectrum of the light that is reflected out of the subject's eye by means of Fast Fourier Transform, to detect a distance between peaks in the reflected signal.

11. The apparatus according to claim 7, wherein the readout equipment is configured to detect light that is reflected out of the subject's eye that is at a resonance frequency of the Fabry Perot interferometer when an optical axis of the readout equipment is parallel with an optical axis of the illumination equipment.

12. The apparatus according to claim 1, further comprising a reference Fabry Perot interferometer comprising at least two reference mirrors, a distance between the reference mirrors being fixed as the intraocular parameter of the subject's eye varies.

13. The apparatus according to claim 12, further comprising a computer processor that is configured to analyze the light that is reflected out of the subject's eye and to account for changes in an angle between an optical axis of the optical device and an optical axis of the illumination equipment and/or the readout equipment, by calibrating measurements that are performed on light that is reflected from the Fabry Perot interferometer using measurements that are performed on light that is reflected from the reference Fabry Perot interferometer.

14. Apparatus comprising:
illumination equipment configured to direct light into an eye of a subject;
an optical device configured to be placed inside the subject's eye, the optical device comprising a first Fabry Perot interferometer comprising at least two mirrors, the interferometer being configured such that a distance between the mirrors varies as an intraocular parameter of the subject's eye varies;
a reference Fabry Perot interferometer comprising at least two reference mirrors, a distance between the reference mirrors being fixed as the intraocular parameter of the subject's eye varies; and
readout equipment configured to detect the light that is reflected out of the subject's eye.

15. The apparatus according to claim 14, wherein the reference Fabry Perot interferometer is in series with the first Fabry Perot interferometer.

16. The apparatus according to claim 14, wherein the first Fabry Perot interferometer is configured such that the distance between the mirrors varies as intraocular pressure of the subject's eye varies.

17. The apparatus according to claim 14, wherein the first Fabry Perot interferometer is configured such that the distance between the mirrors varies as intraocular temperature of the subject's eye varies.

18. The apparatus according to claim 14, wherein the optical device comprises two or more additional mirrors, such that the optical device acts as a plurality of Fabry Perot interferometers in series with each other.

19. The apparatus according to claim 14, wherein the optical device further comprises a retroreflector configured such that light that is transmitted through the first Fabry Perot interferometer is automatically reflected out of the subject's eye.

20. The apparatus according to claim 14, further comprising a reference optical device coupled to the optical device, the reference optical device comprising the reference Fabry Perot interferometer.

21. The apparatus according to claim 20, wherein the reference optical device is coupled to the optical device such that optical axes of the optical device and the reference optical device are parallel to each other.

22. The apparatus according to claim 20, wherein the reference optical device comprises a retroreflector configured such that light that is transmitted through the reference Fabry Perot interferometer is automatically reflected out of the subject's eye.

23. The apparatus according to claim 14, further comprising a computer processor that is configured to analyze the light that is reflected out of the subject's eye such as to identify a resonance frequency of the first Fabry Perot interferometer and to thereby determine the intraocular parameter of the subject's eye.

24. The apparatus according to claim 14, wherein the readout equipment is configured to detect light that is reflected out of the subject's eye that is at a resonance frequency of the first Fabry Perot interferometer when an optical axis of the readout equipment is parallel with an optical axis of the illumination equipment.

25. A method comprising:

directing light into an eye of a subject;

receiving reflected light from an optical device that is placed inside the subject's eye, and that includes:

a Fabry Perot interferometer that includes at least two mirrors, the Fabry Perot interferometer being configured such that a distance between the mirrors varies as an intraocular parameter of the subject's eye varies, and a retroreflector configured such that light that is transmitted through the Fabry Perot interferometer is automatically reflected out of the subject's eye; and analyzing the reflected light to thereby determine the intraocular parameter of the subject's eye.

\* \* \* \* \*